United States Patent [19]

Kiss et al.

[11] Patent Number: 5,006,149

[45] Date of Patent: Apr. 9, 1991

[54] METHOD AND COMPOSITION FOR THE TREATMENT OF FIELD PLANT SEEDS

[75] Inventors: László Kiss, Petöháza; Gyula Justus, Székesfehérvár; József Zsuppán, Abä; Tibor Knollmár, Budapest, all of Hungary

[73] Assignee: Szekszárdi Állami Gazdaság KSZE Növénytermelési Rendszer, Szekszárd, Hungary

[21] Appl. No.: 528,399

[22] Filed: Feb. 27, 1990

Related U.S. Application Data

[63] Continuation of Ser. No. 333,881, Mar. 31, 1989, abandoned, which is a continuation of Ser. No. 226,567, Aug. 1, 1988, abandoned, which is a continuation of Ser. No. 930,969, Nov. 13, 1986, abandoned, which is a continuation of Ser. No. 701,437, Feb. 12, 1985, abandoned, which is a continuation of Ser. No 462,633, Jan. 31, 1983, abandoned, which is a continuation of Ser. No. 271,525, Jun. 8, 1981, abandoned.

[51] Int. Cl.$^5$ .................. A01N 43/08; A01N 54/00
[52] U.S. Cl. ............................. 71/81; 71/65; 71/77; 71/89
[58] Field of Search .................. 71/81, 89, 77, 65

[56] References Cited

U.S. PATENT DOCUMENTS

| 1,173,019 | 2/1916 | Orton | 71/65 |
|---|---|---|---|
| 1,409,126 | 3/1922 | Free | 71/65 |
| 2,894,873 | 7/1959 | Seven | 424/328 |
| 3,031,290 | 4/1962 | Senior | 71/89 |
| 3,038,794 | 6/1962 | Geary et al. | 71/89 |
| 3,158,534 | 11/1964 | Frohberger et al. | 424/328 |
| 3,173,833 | 3/1965 | Frohberger et al. | 424/328 |
| 4,154,596 | 5/1979 | George et al. | 71/89 |
| 4,156,684 | 5/1979 | Crutcher | 71/89 |
| 4,211,550 | 7/1980 | Oyamad et al. | 71/97 |

FOREIGN PATENT DOCUMENTS

| 2736407 | 2/1979 | Fed. Rep. of Germany | 71/97 |
|---|---|---|---|
| 47-28750 | 7/1972 | Japan | 71/89 |

*Primary Examiner*—Frederick E. Waddell
*Assistant Examiner*—Raymond Covington
*Attorney, Agent, or Firm*—Schweitzer Cornman & Gross

[57] ABSTRACT

The invention relates to a process for the treatment of sowing-seeds of field plants in order to increase the reliability of crop yield and to improve the biological properties of the plants emerged. According to the invention the seeds are treated prior to sowing with a neutral or nearly neutral aqueous solution containing an effective amount of a gibberelline derivative $GA_3$ and/or $GA_7$, boron and potassium. The treatment takes generally 3-4 hours.

The invention also relates to a composition applicable in the above process.

7 Claims, No Drawings ns of U.S. Ser. No. 271,525, filed on June 8, 1981, all now abandoned.
METHOD AND COMPOSITION FOR THE TREATMENT OF FIELD PLANT SEEDS This is a continuing application of U.S. Ser. No. 333,881, filed on Mar. 31, 1989, which is a continuing application of U.S. Ser. No. 226,567, filed on Aug. 1, 1988, which is a continuing application of U.S. Ser. No. 070,132, filed on July 6, 1987, which is a continuing application of U.S. Ser. No. 930,969, filed on Nov. 13, 1986, which is a continuing application of U.S. Ser. No. 701,437, filed on Feb. 12, 1985, which is a continuing application of U.S. Ser. No. 462,633, filed on Jan. 31, 1983, which is a continuing application of U.S. Ser. No. 271,525, filed on June 8, 1981, all now abandoned.

The invention relates to a new method and composition for the treatment of field plant seeds in order to improve the biological properties of the plants emerged.

Depending on the plant variety, the biological properties of the emerging plants are influenced to varying extent by various factors, such as climatic, soil and other cultivation conditions. One of the main goals of field plant cultivation is to improve the reliability of crop yield and to exclude the adverse effects of varying climatic and soil conditions already at a stage before sowing by subjecting the sowing-seeds to an appropriate treatment.

The crop yield of wheat, one of the most important field plants, may decrease considerably owing to frost damages during winter. As far as wheat is concerned, beside the increase of frost resistance it is also desirable to improve the homogeneity of germs and the root activity, which involves the improvement of the biological properties of wheat crop and the increase of crop yield.

With corn sown in single seeds it is also an important cultivation factor to increase its frost resistance and to suppress the destruction of germs, increasing thereby the crop yield with relatively low additional investments. In the cultivation of sunflower efforts are made to obtain as uniform a stand as possible and to increase the number of pollinated grains, increasing thereby the crop yield as well. In the cultivation of sugar beet efforts are made primarily to increase their protection against the causes of stem plague; further important aims are the increase of crop yield and the suppression of the harmful nitrogen level.

The preparation of gibberelline derivatives was described first by Stodola et al. [Arch. of Biochem. and Biophys. 54, 240 (1955)]. Ullmann's Encyclopedia der technischen Chemie (Vol. 18, pp. 694–695) reports already on the preparation of 14 gibberelline derivatives ($GA_1$–$GA_{14}$), whereas in "Chemie der Pflanzenschutz- und Schädlingsbekämpfungsmittel" [Vol. II, pp. 401–406 (Springer Verlag, 1970)] the preparation and physical constants of numerous other gibberelline derivatives are described. In practice, gibberelline derivatives have been applied in plant protection primarily to accelerate growth and to stimulate the lengthening processes, i.e. they have been utilized as plant hormones. However, numerous publications report on the unfavourable effects of gibberelline derivatives, therefore the regular use of gibberellines has not become widespread in plant cultivation, not even in combination with other biologically active additives.

The invention aims at the utilization of compositions containing gibberelline derivatives in the treatment of field plant seeds, particularly seeds of wheat, corn, sugar beet, sunflower, alfalfa and other useful crop plants, in order to increase the reliability of crop yield, i.e. to decrease the effect of the variation of climatic and soil conditions on crop yield.

For this purpose certain gibberelline derivatives are applied, in combination with potassium and boron, in aqueous medium in well defined concentrations to treat sowing seeds. This treatment can be performed either simultaneously with the protective dressing of seeds, or prior to or during seed coating. According to the method of the invention the seeds of field plants are treated prior to sowing with 2 to 25% by volume, calculated for the volume of the seeds, of an aqueous solution containing gibberelline derivatives $GA_3$ and/or $GA_7$, potassium and boron in a concentration of 5 to 100 $\mu g/cm^3$, until the seeds get appropriately impregnated with the treating solution. For the treatment of sugar beet and wheat seeds derivative $GA_3$, for the treatment of corn seeds derivative $GA_7$, whereas for the treatment of spring barley, sunflower and alfalfa seeds a (1–2):1 mixture of derivatives $GA_3$ and $GA_7$ is applied in combination with potassium and boron in an aqueous solution, until the seeds are moistened and impregnated appropriately. The treatment takes generally 3 to 4 hours.

The composition which contains gibberelline derivative $GA_3$, potassium and boron is prepared so that one part by weight of crystalline gibberellic acid is admixed with about one part by weight of finely ground potassium hydrocarbonate and 1/5 parts by weight of boric acid, and the resulting mixture is homogenized. The components are applied as commercial products of technical quality.

When preparing an aqueous solution ready for use, the above powder mixture is diluted gradually with water. When a powder mixture which contains 1 g of 100% crystalline $GA_3$ is applied as starting substance, aqueous solutions applicable for seed treatment with an active agent concentration of 100 $\mu g/cm^3$ or 10 $\mu g/cm^3$, respectively, are obtained upon diluting the powder mixture with 10 liters or 100 liters of water. Instead of water, aqueous solutions of plant protecting seed dressing agents free of heavy metal salts can also be applied to dilute the solution.

To prepare a composition which contains gibberelline derivative $GA_7$, potassium and boron, one part by weight of powdered $GA_7$ is dissolved in about 100-fold amount of acetone, and then 1/5 parts by weight of potassium hydroxide are added as a 20% aqueous solution. The potassium hydroxide solution is introduced gradually into the acetone solution. Thereafter boric acid is added to the aqueous-acetonic solution in an amount sufficient to lower its pH to 7 from the initial value of 10, and the resulting solution is freeze-dried. This dry composition is converted into aqueous solutions applicable for seed treatment as described above. According to our experiences it is preferred for the aqueous solution of the active agent composition to be completely free of organic solvents or to contain only trace amounts of organic solvents. An important precondition of the treatment is that the gibberelline derivative should remain stable upon storage, which can be ensured by the combinations according to the invention.

Thus, in accordance with the invention, the seeds are treated so that a solution with an active agent content of 5 to 100 $\mu g/cm^3$ is prepared from the above composition, and one part by volume of the seed to be treated is contacted with 2 to 25% by volume of the solution. The seeds absorb the solution generally within 3-4 hours.

The seed treating operation can be combined to advantage with the protective dressing of seeds. In this instance the composition according to the invention is admixed with the seed dressing agent, and then the conventional dressing technique is applied. An important precondition of the simultaneous dressing and treatment of the seeds is that the seed dressing agent must be free of heavy metal salts. Of the applicable dressing agents e.g. tetramethyl-thiuram disulfide, Fundazol, Quinolate and Dithan M-45 [(manganese, zinc)-ethylene-bis(dithiocarbamate] are to be mentioned.

According to a further preferred method of the invention the seed treatment is combined with the coating of the seeds. In the up-to-date sowing techniques the seeds to be sown are more and more frequently treated with coating agents in order to ensure a uniform grain size and to protect the seeds. Seed coating is performed preferably according to the well known tablet coating technologies of the pharmaceutical industry. The dressed and coated seeds can be dried and stored.

It is advantageous to wet the seeds prior to both dressing and coating, in order to bring them into soil-wet state. According to the invention the seeds are wetted with the composition which contains the gibberelline derivative.

Of course, seed dressing or seed coating can also be performed so that the composition according to the invention is added to the dressing or coating agent and the composition is applied onto the seeds together with the dressing or coating substance. The seeds are then dried. One skilled in the art can easily select the most appropriate method of application.

As a result of the treatment according to the invention e.g. in the cultivation of sugar beets the difference between the number of sown and emerged stems decreases considerably, and, beside the increase of stem number, the sugar beets get less damaged by the causatives of stem plague. When wheats are treated according to the invention, the frost resistance of the plants increases, the structure of ears improves, furthermore the grain number of the ears, the thousand-grain weight and the gluten content increases. On corns the treatment results in the increase of frost resistance, and good individual crop yields can be attained. Based on field tests, similar good results can be obtained for sunflower, alfalfa and spring barley as well.

The invention is elucidated in detail by the aid of the following non-limiting Examples.

EXAMPLE 1

Treatment of sugar beet sowing-seeds

Prior to the treatment the glomeruli which contain more germs are always subjected to abrasion in order to obtain single-germ glomeruli.

(A) 25% by volume of a composition containing 50 $\mu g/cm^3$ of gibberelline derivative $GA_3$, potassium and boron, prepared as described above, are applied onto one part by volume of sugar beet glomeruli (variety M-102), pre-treated by abrasion. The composition also contains tetramethyl-thiuram disulfide seed dressing agent. The glomeruli are allowed to stand in the composition for 3-4 hours; during this period the glomeruli absorb the treating solution.

(B) One part by volume of sugar beet glomeruli (M-102 variety), pre-treated by abrasion, is treated with an aqueous composition containing 100 $\mu g/cm^3$ of gibberelline derivative $GA_3$, boron and potassium, prepared as described above. 20% by volume of the solution are applied for the treatment. The glomeruli absorb the solution within a period of 3-4 hours.

(C) Abrased sugar beet glomeruli (Beta-monoploi M-1 variety) are treated with a composition containing 50 $\mu g/cm^3$ of gibberelline derivative $GA_3$, potassium and boron, prepared as described above. A seed dressing agent containing tetramethyl-thiuram disulfide is also added to the solution prior to the treatment. 20% by volume of the solution are applied for the treatment of one part by volume of the glomeruli. The glomeruli absorb the solution within about 3 hours and reach a soil-wet state. At this stage the glomeruli are filled into a dragée pan, coated with a coating agent applied in sugar industry and then dried. These treated seeds are then sown.

(D) Abrased glomeruli of Beta-monoploi M-1 sugar beet are dressed with a seed dressing agent containing tetramethylthiuram disulfide in a conventional manner. After dressing the glomeruli are filled into a dragée pan and coated there with a coating agent applied in the sugar industry, to which a treating solution according to the invention, containing 50 $\mu g/cm^3$ of gibberelline derivative $GA_3$, was added in an amount of 20% by volume calculated for the volume of the glomeruli. These treated seeds are then sown.

The treated seeds were applied with good results in tests performed on large parcels. Before the tests the seeds were treated according to the following methods:
Method 1: the glomeruli were treated according to the invention and then sown;
Method 2: the glomeruli treated according to the invention were coated first and then sown;
Method 3: the glomeruli were coated with a coating agent also containing the composition according to the invention and then sown.

The results of the tests are listed in Table 1. It should be noted that the percentage stem density significantly supersedes that of the controls in all of the three methods examined.

It has been observed in the large parcel tests that, due to the explosive plant emergence, the soil-borne causatives of stem plague cannot attack the sugar beet plants which emerge from the treated seeds. The crop yields also increased significantly (the average crop yield observed on the treated area is 46,260 kg/hectare, in contrast to the yield of 43,060 kg/hectare observed on the control parcels).

TABLE 1

Examination of the effects of sugar beet treatment (large parcel tests)

| | Method of seed treatment | | |
|---|---|---|---|
| | 1 | 2 | 3 |
| Number of stems/10 meters | | | |
| treated | 63 | 46 | 49 |
| control | — | 31 | — |
| Number of stems/hectare | | | |
| treated | 138,600 | 101,200 | 107,800 |
| control | — | 68,200 | — |
| Index, % | | 148 | |
| Number of stems/10 meters | | | |
| treated | 68 | 70 | 77 |
| control | — | — | 65 |
| Number of stems/hectare | | | |
| treated | 136,000 | 154,000 | 169,000 |
| control | — | — | 143,000 |
| Index, % | | | 118 |

TABLE 1-continued

Examination of the effects of sugar beet treatment (large parcel tests)

| | Method of seed treatment | | |
|---|---|---|---|
| | 1 | 2 | 3 |
| Number of stems/10 meters | | | |
| treated | 96 | 69 | 63 |
| control | 47 | — | — |
| Number of stems/hectare | | | |
| treated | 211,200 | 151,800 | 138,000 |
| control | 103,400 | — | — |
| Index, % | | 204 | |

Remark: The stem number data relate to the small parcels.

EXAMPLE 2

Treatment of corn sowing-seeds (a) Corn seeds (NKPX-20 variety) are treated with a composition according to the invention containing 20 μg/cm³ of gibberelline derivative GA₇, potassium and boron together with tetramethyl-thiuram disulfide dressing agent. The solution is applied onto the seeds in an amount of 12% by volume calculated for the volume of the seeds. The treated seeds are allowed to stand for 3-4 hours, and then sown.

(b) Corn seeds (SzeCs-369 variety) are treated with a composition according to the invention containing 20 μg/cm³ of gibberelline derivative GA₇, potassium and boron. The solution is applied onto the seeds in an amount of 12% by volume calculated for the volume of the seeds. The seeds absorb the solution within 3-4 hours. Corn seeds of JX-62 variety are also treated in the same manner.

The effect of the treatments is examined by the following tests:

(A) 400 seeds were maintained for 6 days at 6° C. and then placed into a phytotrone for 10 days at 20° C. The seeds were germinated in darkness. The perfect germs, the malformed germs and the dead seeds were counted, and the percentage ratio of perfect germs to the total number of seeds was regarded as percentage germination. The germs were weighed, and the percentage increase in germ weight was calculated in relation to the controls. The results are listed in Table 2. The treatments were performed as described in Example 2 on corn seeds of NKPX-20, SzeCs-369 and JX-62 varieties. Corn seeds germinated in a common water culture were used as controls. The figures indicate that the treatment has a beneficial effect on germination even under optimum laboratory conditions.

(B) The above test was also performed in light, using test groups each consisting of 10 seeds. The results were evaluated by determining the development grade of the germs and measuring their lengths. The results are listed in Table 3. The data of Table 3 indicate again that the effect of the treatment is significant even under laboratory conditions.

(C) Treated corn seeds of JX-62, NPKX-20 and SzeCs-369 varieties were germinated in a phytotrone under the conditions described above, and the diameter and weight of the germs were compared to those of the controls. The average diameter of the germs developed from the control seeds was 2.00 mm, in contrast to the value of 3.00 mm observed for the treated samples, and an increase of about 10% in germ weight could be observed in comparison to the controls. The effect of the treatment was not only a lengthening of the germs; morphologically proportional germs were developed.

(D) Large-parcel tests were performed to compare the stem number of the treated and control plants and the pistillate inflorescence, in particular the structure of corn ears. From the data listed in Table 4 it appears that the variation of the Cold-test value and the percentage field stem realization are in a firm correlation with each other. The observed phenomenon is specific to the variety and depends on the cold resistance of the individual varieties.

TABLE 2

Results of corn germination tests

| | No. of germs | | No. of malformed germs | | No. of dead seeds | | Percentage germination | | Total weight of germs,g | | Germ weight, % related to the controls | |
|---|---|---|---|---|---|---|---|---|---|---|---|---|
| Variety | T | C | T | C | T | C | T | C | T | C | T | C |
| NKPX-20 | 317 | 344 | 14 | 28 | 15 | 28 | 92.75 | 86.00 | 410.94 | 367.26 | 111.9 | 100.0 |
| SzeCs-369 | 393 | 387 | 6 | 11 | 1 | 2 | 98.25 | 96.75 | 422.18 | 418.57 | 100.9 | 100.0 |

T = treated; C = control

TABLE 3

Germination of corn in light under laboratory conditions

| | Variety | | | |
|---|---|---|---|---|
| Development state and | NKPX-20 | | SzeCs-369 | |
| length of the germ | treated | control | treated | control |
| Funneliform green leaf primordium | | | | |
| number | 5 | — | 4 | — |
| average length, cm | 7.4 | — | 6.75 | — |
| Closed green leaf primordium | | | | |
| number | 3 | 3 | 2 | — |
| average length, cm | 4.3 | 4 | 3.75 | — |
| Green germ | | | | |
| number | 2 | 2 | 3 | 5 |
| average length, cm | 2.0 | 1 | 2.5 | 2 |
| White germ | | | | |
| number | — | 5 | 1 | 5 |

TABLE 4

Evaluation of Cold-test and experimental stem number under field conditions

| | | | Stem realization under field conditions (number of seeds sown: 59578/hectare) | | | | | | | |
|---|---|---|---|---|---|---|---|---|---|---|
| | Cold-test | | I | | II | | III | | Average | |
| Variety | T | C | T | C | T | C | T | C | T | C |
| AUJ-256 | 96.5 | 95.0 | 54000 | 53800 | 51750 | 51750 | 57500 | 58500 | 55375 | 55075 |
| NKPX-20 | 97.0 | 96.5 | 53750 | 53000 | 55250 | 53000 | 51250 | 51000 | 54500 | 53687 |

TABLE 4-continued

| | Evaluation of Cold-test and experimental stem number under field conditions | | | | | | | | | |
|---|---|---|---|---|---|---|---|---|---|---|
| | | | Stem realization under field conditions (number of seeds sown: 59578/hectare) | | | | | | | |
| | Cold-test | | I | | II | | III | | Average | |
| Variety | T | C | T | C | T | C | T | C | T | C |
| JX-20 | 91.2 | 82.5 | 51000 | 49000 | 52000 | 51250 | 51000 | 43500 | 51500 | 47812 |

T = treated; C = control

The data listed in Table 5 indicate that as a result of the treatment the perimeter of the ears increases, the number of rows on the ears increases in proportion to the increase in perimeter, and the length of the ears increases as well.

TABLE 5

| | Analysis of the ear structure of corn | | | | | |
|---|---|---|---|---|---|---|
| | Number of rows on the ears | | Perimeter of ears, mm | | Length of ears mm | |
| Variety | T | C | T | C | T | C |
| AUJ-256 | 15.1 | 14.0 | 55.0 | 47 | 192 | 156 |
| NKPX-20 | 16.4 | 14.0 | 73.0 | 47 | 232 | 192 |
| JX-20 | 16.0 | 14.8 | 63.0 | 58 | 214 | 204 |

T = treated; C = control

The increase in the perimeter of the ears, and, consequently, the increase in the number of rows can be attributed to the specific effect of the composition according to the invention that it acts on the pistillate inflorescence of corn in the initial development stage, and, owing to the higher chlorophyll activity, a more robust ear structure may develop during the growth season. This fact is also proved by the data of Table 6, in which the favourable changes in thousand-seed weight and useful substance content are shown.

TABLE 6

| | Thousand-seed weight, g | | Starch, % | | Crude protein, % | |
|---|---|---|---|---|---|---|
| Variety | T | C | T | C | T | C |
| AUJ-256 | 302 | 294 | 73.1 | 70.1 | 9.1 | 10.6 |
| NKPX-20 | 400 | 398 | 69.1 | 70.3 | 10.4 | 9.4 |
| JX-62 | 282 | 266 | 68.0 | 70.2 | 12.5 | 8.2 |

EXAMPLE 3

Treatment of wheat sowing-seeds

Wheat seeds (MV-4 variety) are treated with an aqueous solution according to the invention containing 20 $\mu g/cm^3$ of gibberelline derivative $GA_3$. Prior to the treatment a desired amount of Quinolate dressing agent is added to the solution. The solution is applied onto the seeds in an amount of 2% by volume related to the volume of the seeds.

Wheat seeds of Rana-2 and GK-Tiszatáj varieties are treated similarly with an aqueous solution containing 20–50 $\mu g/cm^3$ of active agent, admixed with Dithan M-45 dressing agent prior to application.

The results of the treatments were examined in the following tests:

In a large-parcel test seeds of wheat (MV-4 variety) were sown on 15 hectares. 1000 seeds weighed 44.5 g, the utility grade of the seeds was 95.8%.

The number of seeds sown on one hectare was 6,471,573, of which 6,458,426 were able to germinate.

The following results were obtained after the emergence of the plants:

Actual number of stems: 5,740,000/hectare.

Ratio of the actual stem number to the seeds sown: 85.2%.

Ratio of the actual stem number to the utility grade of the seeds: 89%.

The stand overwintered in a stage of 4–6 leaves, and yielded a crop of 4,230 kg/hectare. On the control parcel a crop yield of 3,950 kg/hectares was obtained.

In the biological tests the following parameters were determined on the seedlings developed from the treated and control seeds:

Homogeneity of the germs (ratio of identical germs during a germination period of 10 days):
treated: 73.2%
control: 49.5% intensity of photosynthesis (dry weight of substance synthetized at 10° C. within 24 hours, mg/100 plants in the two-leaf stage):
treated: 1107 mg
control: 852 mg Root activity (specific activity of ribosomal nucleic acid, cpm/$P^{32}$ built in within 24 hours at 3° C.):
treated: $9.9 \times 10^3$
control: $8.7 \times 10^3$ Actual frost resistance without acclimatization ($LT_{50}$):
treated: $-14.1°$ C.
control: $-10.7°$ C.

It appeared in the large-parcel tests that, with no regard of the variety, the stooling of wheat improved to varying degrees, furthermore the number of ears per meter and the crop yield increased as well. These data are summarized in Table 7.

TABLE 7

| Variety | Stooling index, % | Number of ears per meter | | Index % | Crop yield Kg/ha | | Index % |
|---|---|---|---|---|---|---|---|
| | | T | C | | T | C | |
| MV-4 | 111.6 | 120.6 | 116.2 | 104.0 | 7110.0 | 6280.0 | 113.2 |
| MV-4 | 127.7 | 104.0 | 78.6 | 133.4 | 6265.0 | 5879.0 | 106.5 |
| MV-4 | 138.1 | 125.6 | 93.2 | 136.9 | 6223.0 | 4852.5 | 128.2 |
| Rana-2 | — | 89.8 | 71.4 | 125.9 | 6697.0 | 5198.0 | 128.8 |
| GK-Tiszataj | — | 105.0 | 77.2 | 136.1 | 6216.0 | 5436.7 | 114.3 |

The results observed in the large-parcel tests also indicate that the thousand-seed weight (expressed in grams) increases, and the bakery value of the individual wheat varieties improves. The thousand-seed weights are listed in Table 8, and the data characteristic of bakery value are given in Table 9.

TABLE 8

| | Thousand-seed weights, g | |
|---|---|---|
| Variety | Treated | Control |
| MV-4 | 52.2 | 41.0 |
| Rana-2 | 42.8 | 40.2 |
| GK-Tiszataj | 40.8 | 36.2 |

TABLE 9

Data characteristic of bakery value

| Variety | Moisture content, % | Bakery value | Amount of wet gluten | Spreadability of gluten | Hagberg's drop number |
|---|---|---|---|---|---|
| Rana-2 (treated) | 17.6 | 70.2-$A_2$ | 32.0 | 3.5 | 265.0 |
| Rana-2 (control) | 20.2 | 69.6-$B_1$ | 30.25 | 2.5 | 281.0 |
| MV-4 (treated) | 15.9 | 85.3-$A_1$ | 37.5 | 3.5 | 321.5 |
| MV-4 (control) | 16.4 | 80.8-$A_2$ | 35.75 | 3.0 | 313.5 |
| GK-Tiszataj (treated) | 17.4 | 100.0-$A_1$ | 39.25 | 1.25 | 320.0 |
| GK-Tiszataj (control) | 17.2 | 89.5-$A_1$ | 36.75 | 2.5 | 326.5 |

It appears from Table 9 that the amount of wet gluten increases, and the spreadability of gluten decreases. There is no significant difference in the Hagberg's drop number, which can be attributed to the fact that the treatment did not modify the α-amylase enzyme activity of the harvested crop, consequently the seeds to be utilized as foodstuffs contain no residues of the treating agent.

As a result of the treatment of wheat not only the sowing in excess can be avoided, which results in considerable savings, but it makes possible the timing of the emergence of the plants as well. Namely, the wheat treated according to the invention reaches the 4-6 leaves' development stage within about 2 weeks, practically independently of weather conditions, which is the most favourable with respect to overwintering.

EXAMPLE 4

Treatment of spring barley sowing-seeds

Spring barley sowing-seeds are treated directly before sowing with a mixture of Quinolate (a seed dressing agent) and a composition according to the invention which contains a 2:1 mixture of gibberelline derivatives $GA_7$ and $GA_3$ in a total concentration of 20 μg/cm³. The solution is applied in an amount of 10% by volume calculated for the volume of the seeds. The treated seeds are allowed to stand for 3 hours. Dithane M-45 can also be applied as seed dressing agent instead of Quinolate. As a result of the treatment the ear axis can be lengthened, whereupon the number of seeds per ear increases, and the position of the stooling node increases tangentially.

EXAMPLE 5

Treatment of sunflower sowing-seeds

Sunflower seeds (GK-70 variety) are treated with an aqueous solution according to the invention, containing a 1:1 w/w mixture of gibberelline derivatives $GA_7$ and $GA_3$ in a total concentration of 50 μg/cm³. The solution is applied in an amount of 15% by volume calculated for the volume of the seeds. The seeds absorb the solution within about 3-4 hours. In a parallel test Fundazol (a seed dressing agent) is also added to the treating liquid prior to treatment in an amount of 0.3% calculated for the weight of the seeds. In other respects the treatment is performed as described above.

The treated seeds were examined in phytotrone. The results observed are listed in Table 10.

TABLE 10

|  | Treated | Control |
|---|---|---|
| Wet weight, g | 95.310 | 71.642 |
| Number of uniformly developed plants | 27 | 21 |
| Dry weight, g | 11.897 | 8.417 |

The phytotrone tests were repeated under field conditions. According to our experiences the plant stand was more uniform, the diameter of the productive area (i.e. of the disc) was greater, and fertilized seeds could be found even in the centre of the disc. This phenomenon illustrates that there is an increased chlorophyll activity during the growth season, and the possibilities of crop failure are greatly reduced.

The sunflower plants emerge more quickly, which involves the advantage that animals gnaw away the plants to a lesser extent. In the three-leaves stage the first hairy leaves appear on the plant, thereafter the animals do not gnaw away the plant, thus, as a result of the treatment according to the invention the plants are less exposed to this danger.

EXAMPLE 6

Treatment of alfalfa sowing-seeds

Alfalfa sowing-seeds (synalfa variety) are treated with an aqueous composition according to the invention which contains a 1:1 w/w mixture of gibberelline derivatives $GA_3$ and $GA_7$ in a total concentration of 50 μg/cm³. The treating solution is applied in an amount of 10% by volume calculated for the volume of the seeds. After 4 hours of absorption the seeds are ready for sowing.

The treatment promotes the cultivation of alfalfa. It is known that on areas with drier climatic conditions alfalfa cannot be sown in the autumn at all, since the emergence of alfalfa is rather slow, and it is improbable that the plants become sufficiently strong and resistant by winter. As a result of the treatment according to the invention the alfalfa seeds can be sown even in the autumn without any risk, thus the crop yield can be doubled already in the first year. The tendency of increase in crop yield is durable.

What we claim is:

1. A process for the treatment of sowing seeds of field plants selected from the group consisting of wheat, corn, sunflower, sugar beet and alfalfa, to improve the biological properties of the plants, comprising the step of treating the seeds prior to sowing and germination with 2-25% by volume calculated for the volume of the seed of a neutral or nearly neutral aqueous solution of the composition containing gibberelline derivatives $GA_3$, $GA_7$ or a mixture thereof, potassium in the form of potassium hydrocarbonate or potassium hydroxide and boron in the form of boric acid, in a concentration of 5-100 μg/cm³.

2. A process as claimed in claim 1 wherein the seeds are maintained in the treating solution for 3-4 hours.

3. A process as claimed in claim 1, wherein the aqueous solution is applied onto the sowing-seeds prior to seed coating or prior to applying any other coating agent onto the seeds.

4. A process as claimed in claim 1, wherein the aqueous solution is applied onto the sowing-seeds during seed coating, in a mixture with the seed coating substance.

5. A process for the treatment of sowing-seeds of sugar beet or wheat plants as claimed in claim 1 wherein the gibberelline derivative is $GA_3$.

6. A process for the treatment of sowing-seeds of corn plants as claimed in claim 18, wherein the gibberelline derivative is $GA_7$.

7. A process for the treatment of sowing-seeds of sunflower or alfalfa plants as claimed in claim 1 wherein the gibberelline derivatives are a (1–2):1 mixture of $GA_3$ and $GA_7$.

* * * * *